United States Patent [19]

Kauffman

[11] 3,940,260

[45] Feb. 24, 1976

[54] METHOD OF ERADICATING WOODY PLANTS

[75] Inventor: Ralph I. Kauffman, North Hills, Pa.

[73] Assignee: Amchem Products, Inc., Ambler, Pa.

[22] Filed: Oct. 8, 1971

[21] Appl. No.: 187,846

[52] U.S. Cl. .................. 71/110; 71/94; 71/107; 71/108; 71/109; 71/113; 71/115; 71/116; 71/117
[51] Int. Cl.² ........................................ A01N 9/26
[58] Field of Search .................. 71/94, 113, 115

[56] References Cited
UNITED STATES PATENTS

| | | | |
|---|---|---|---|
| 3,589,891 | 6/1971 | Mocotte et al. | 71/113 |
| 3,671,215 | 6/1972 | Bellsmith et al. | 71/115 |

OTHER PUBLICATIONS

Aldred, Proceedings, Nineteenth Annual Meeting Southern Weed Conference, 1–1966, pp. 316–321.

Kirch et al., Proceedings Twentieth Annual Meeting of Southern Weed Conference, 1/1967, pp. 251–255.

Primary Examiner—Glennon H. Hollrah
Attorney, Agent, or Firm—Ernest G. Szoke; Michael E. Zall; Howard S. Katzoff

[57] ABSTRACT

Eradication of oak and other woody plants is obtained through a synergistic effect derived from the application of herbicides of two different groups wherein the first group consists of a chlorinated aliphatic acid which can be trichloroacetic acid or 2,2-dichloropropionic acid; and the second group consists of 2,4-dichlorophenoxyacetic acid, 2,4,5-trichlorophenoxyacetic acid, 2,4-dichlorophenoxypropionic acid, 2,4,5-trichlorophenoxypropionic acid, 2-methyl-4-chlorophenoxyacetic acid, 3,6-dichloro-o-anisic acid, 2,3,6-trichlorobenzoic acid and 4-amino-3,5,6-trichloropicolinic acid.

4 Claims, No Drawings

METHOD OF ERADICATING WOODY PLANTS

DETAILED DESCRIPTION

According to this invention there is provided a method for eradicating brush and other woody plant growth from overland rights-of-way, along roadsides, railroad roadbeds, drainage and irrigation ditches, rangelands and other non-crop lands by applying in conjunction two or more herbicides.

More particularly, this invention concerns a method for killing brush by the directed application of two or more herbicides, separately or in admixture, to wet the foliage with one herbicidal component and the ground area under the foliage with a second herbicidal component.

This invention further concerns a combination product comprising a herbicidal spray solution having two herbicidal components one of which, Component A, contains a herbicide selected from the group consisting of a trichloroacetic acid (TCA), its salts and esters and 2,2-dichloropropionic acid (dalapon), its salts and esters; and the other of which, Component B, contains a herbicide selected from the group consisting of 2,4-dichlorophenoxyacetic acid (2,4-D), its salts and esters; 2,4,5-trichlorophenoxyacetic acid (2,4,5-T), its salts and esters; 2,4-dichlorophenoxypropionic acid (2,4-DP), its salts and esters; 2,4,5-trichlorophenoxypropionic acid (2,4,5-TP), its salts and esters; 2-methyl-4-chlorophenoxyacetic acid (MCPA), its salts and esters; 3,6-dichloro-o-anisic acid (dicamba), its salts and esters; 2,3,6-trichlorobenzoic acid (TBA), its salts and esters; and 4-amino-3,5,6-trichloropicolinic acid (picloram), its salts and esters.

The control of brush and woody plants is a problem in many areas, particularly utility rights-of-way, such as power transmission lines, telephone lines, gas and oil pipelines, etc., along irrigation and drainage ditches, along roadsides and railway roadbeds and for the selective elimination of undesirable species in gamelands, parklands, etc., thereby to permit better development of desired species, particularly, in such areas where climate and heavy rainfall cause prolific growth.

Brush which needs control and preferably eradication includes a great number of plants such as, various maples, willows, oaks, elms, ashes, locusts, hickories, persimmons, sumacs, pines, firs, spruces, hemlocks, cedars, sassafras, sour gums and the like. A particularly difficult control problem arises when various brush and vines (briars) growing in the same area reach for the sun, resulting in a high intertwine and almost impenetrably dense growth. Additional problems are encountered where the natural brush mix includes a significant proportion of oak and other species which are not easily controlled by chemical methods. Control of such brush growth has met with some success by the application of chemicals and, particularly the application of 2,4-dichlorophenoxyacetic acid and 2,4,5-trichlorophenoxyacetic acid, their esters and salts and mixtures. Solutions of these chemicals are ordinarily sprayed on the foliage by means of power or hand-operated equipment or by aircraft (helicopter or fixed-wing aircraft). Disadvantages to this type treatment is that, to date, these chemicals have given only incomplete control of brush, particularly as regards the hard-to-kill species notably the oak, ash and maple varieties. Control of these and other hard-to-kill species requires repeated applications, as well as cutting. Varieties of conifers have also been found to be highly resistant to these treatments. Previous attempts have been made to effect better brush control with the phenoxy derivatives by applying them in combination with trichloroacetic acid (as the sodium salt). Thus, for example, control of maple by such combination of chemicals has been reported by William S. Hoff (Down to Earth No. 8 (1), pages 5 to 7, 1952). During the period 1962–65 J. R. Aldred evaluated the effect of trichloroacetic acid (as the sodium salt) in brush control when added to various 2,4-dichlorophenoxyacetic acid and 2,4,5-trichlorophenoxyacetic acid esters and amine salts in very extensive experiments on the rights-of-way of the Tennessee Valley Authority's transmission lines (Procedure of SWC, pages 316–321, 1966). The chemicals were applied by helicopter and by power sprayer from a truck, and also by hand. From these tests Aldred concluded there was no advantage in using trichloroacetic acid (as the sodium salt) with the phenoxy derivatives, since the latter when used alone gave an equal amount of kill and the results obtained by adding trichloroacetic acid (as the sodium salt) in combination with the phenoxy herbicides did not warrant further work with these combinations on brush control. Others have experienced similar lack of promise in these combinations.

It has now, however, been discovered that thorough and lasting brush control and eradication of many of the hard-to-kill species can be accomplished with a combination of trichloroacetic acid or its salts or esters, or 2,2-dichloropropionic acid, its salts and esters when applied in combination with a chlorophenoxyaliphatic acid, dicamba, TBA or picloram by applying these herbicides in such a manner that the foliage receives a dosing of one or more of the herbicides comprising Component B as described above, while the trichloroacetic acid and/or 2,2-dichloropropionic acid herbicide (Component A) is applied to the ground over the rooth system of the brush. This can be accomplished by spraying a combination of these products in a suitable liquid carrier in such a way that a portion of the spray solution contacts the foliage while the remainder goes onto the ground over the root system. This can be conveniently done by applying the spray solution having one or more of the herbicidal materials of Component A and one or more of the herbicidal materials of Component B in solution or suspension so that when the spray solution is applied in such a manner as to be directed from above the brush down through the foliage to the ground producing sufficient contact with the foliage to moisten it while permitting the bulk of the spray solution to contact the ground over the roots. This technique emphasizes spray application to the foliage at low rates and application to the ground area at higher rates. Similar results can also be accomplished by split application whereby the Component A herbicide is applied to the ground and the Component B herbicide is applied to the foliage. Where split applications are employed the second application should be made as soon as practicable after the first and in any case within about one or two weeks. Either compound can be applied first, though for practical reasons it is generally best to make the ground application first.

Still a further unexpected and advantageous result of the combination treatments of this invention is the discovery that marked improvement in brush kill is obtained even when the treatment is applied during periods of retarded growth and in early Spring and late Fall. Treatments according to this invention applied in early Spring and in late Fall gave comparable results to those obtained from applications during the normal growing season. Conventional herbicide treatments for brush control show a distinct decrease in efficiency when applied before or after the main growing season. The treatments of this invention by providing pre- or post-growing season results produce the highly desirable result of lengthening the spray season.

Accordingly, it is an object of this invention to provide an effective, low-cost process for eradicating woody plants (brush), particularly oak, ash and red maple. The compositions and methods of this invention are especially effective against certain difficult oak species, for example the species Quercus spp. Another object of this invention is to dispense with repeated applications or cuttings in brushkilling. It is a further object of this invention to provide a brushkilling process that is equally effective for pine, maple, oak and other woody vegetation, such as is ordinarily found in a random mix of brush in rights-of-way. Still another objective of this invention is to use two types of herbicides for brushkilling in such a way that they mutually reinforce their individual action on woody plants and their killing effect to provide a synergistic herbicidal effect which substantially exceeds the effect expected on the basis of their activity as an additive effect. A further object of this invention is to provide a brushkilling method that provides complete eradication of oak and other woody plants in utility rights-of-way and similar areas where such plants are undesirable without the need for repeated application or supplementary cutting operations.

One method of application according to this invention is to apply a combination of herbicides in liquid form using conventional spray techniques but employing a spray nozzle with large openings and applying at relatively low pressures. When spraying with this setup the foliage is covered only with a light spray and the spray pattern is directed mainly toward the ground. Another method of application is to spray down through the brush. This can be accomplished from a platform on a spray truck using a spray gun that allows the spray to be directed downward through the brush thereby covering the foliage only lightly with most of the spray going on through to the ground. The liquid herbicide mixture is sprayed down through the foliage to the ground thereby wetting the foliage in the process of getting the herbicidal product onto the ground. This method is facilitated by having the operator on a tower or platform so that the spray source is elevated above the foliage to be sprayed thereby permitting the spray operator, when applying the liquid, to spray down through the foliage.

In conventional spraying the spray is applied to the foliage until it is thoroughly wet, that is until run-off. According to the process of this invention the spray is applied to the foliage as a light application, sufficient to barely wet the foliage and the remainder of the spray application is directed to the ground. While this may result in some wetting of the canes or stems of the brush, this is not necessary according to the process of this invention.

For maximum results a split application could be employed whereby the Component B herbicide is directed to the foliage only and the trichloroacetic acid or 2,2-dichloropropionic acid herbicide (Component A) is directed to the ground only. This can be done in successive applications or by the use of two separate spray nozzles. However, for convenience it has been found best to use a single mix spray as described above, whereby the application is made by spraying down through the foliage to the ground, wetting the foliage in the process. It has also been found that unlike conventional spraying where it is desirable to use a small nozzle tip, usually a No. 6 (6/64 inch opening) with high pressure (about 650 psi) to give a finer type of spray so as to thoroughly wet the foliage; the process of this invention utilizes a larger nozzle, usually about a No. 10 (10/64 inch opening) and lower pressure (about 400 psi or less). This will result in heavier spray particles which drop more quickly to the ground and only incidentally wet the foliage while passing through. Such coarser spray pattern will penetrate through the foliage to the ground much better than the fine spray from the smaller nozzle tip and higher pressure using conventional techniques.

Additionally, it is customary in spraying brush by conventional techniques to increase the volume used as the size of the brush increases. Thus, it is necessary to adjust the total volume of spray solution applied in accordance with the size and density of the brush. According to the process of this invention the rate of application is substantially independent of the height or density of the brush and excellent results can be obtained when the herbicidal combinations of this invention are properly applied in accordance with the invention at dosage rates determined on a per acre basis depending upon the choice of components regardless of the size or density of the brush.

The herbicidal components of this invention can be formulated as high strength concentrates with both essential components combined in a single concentrate mixture or blend of compatible components. Or, they can be formulated as separate concentrates to be separately applied in conjunction one with the other, or combined at the time they are diluted to the final spray concentration, i.e. as tank mixes.

The total amount of active ingredient will ordinarily be present in the concentrate in amounts ranging between about 50 and 95% by weight whether as a single formulation, combining the two active components, or as separate concentrates containing one or more active herbicidal substance in each concentrate. The remaining portion of the concentrate will consist of one or more of the conventional herbicidal adjuvants, such as water, petroleum distillates or other organic solvent carriers, surface active dispersing agents and finely divided inert solids. The concentrates thus formulated are subsequently diluted for use with additional inert carrier to produce the ultimate treating solution.

The exact concentration of the herbicidal components to be employed in accordance with the process of this invention for the treatment of oak and other woody plant species may be varied within a fairly wide range provided the required dosage of active components are supplied to the foliage and the ground around over the root system of the plant, respectively. The concentration of active ingredients in the herbicidal concentrates can also vary widely as indicated above, so long as the final spray composition is made up and applied so as to provide the required active dose.

In applying the herbicidal compositions according to the process of this invention the dosages will vary depending upon the particular selection of ingredients for Component A and Component B and the combination of these components, though ordinarily the following amounts will be required for best results.

In using TCA, generally in the salt form there is optimally utilized about 60 lbs/acre of active ingredient though lower amounts can also be utilized with only slight loss in effectiveness, even amounts as low as 35 to 40 lbs/acre. If the TCA esters are utilized, somewhat lower amounts can be employed, and in particular ethylene glycol bis(trichloroacetate) can be used in amounts of 40 lbs/acre or less.

When using the dalapon or dalapon ester there is optimally employed about 12 lbs/acre, though as low as 8 lbs/acre used with a Component B herbicide as described herein will give effective eradication of most woody plants.

In the case of the Component B materials, where the active ingredient is dicamba in either its salt, ester or acid form, there is optimally utilized about 6 lbs/acre, though amounts as low as 4 lbs/acre can also be employed. Particularly useful is the dicamba oil soluble amine form.

In the case of picloram amounts of about 1 to about 1.5 lbs/acre are suitably employed in either the salt or ester form and lower amounts in the order of three-fourths lb/acre can even be used to achieve effective results.

With TBA there is ordinarily required about 12 lbs/acre, though 8 or 10 lbs/acre will also provide sufficient elimination of woody plant species when used in combination as provided for in this invention.

In the case of the phenoxy herbicides, 2,4-D should be employed in amounts of about 24 lbs/acre in either its acid, salt or ester forms, though lower amounts can be employed, even as low as about 16 lbs/acre. When 2,4,5-T is employed it should be utilized in amounts of about 8 lbs/acre, though as little as 6 lbs/acre can also be employed. 2,4-DP and 2,4,5-TP should be utilized in amounts corresponding to those for 2,4-D and 2,4,5-T. MCPA should likewise be utilized in amounts corresponding to those for 2,4-D and 2,4-DP. In the case of mixtures of the phenoxys they are optimally used in equal proportions. Thus, for example, a particularly effective combination for use in this invention can be made by using a 1 : 1 ratio of 2,4-D and 2,4,5-T applied at a rate of about 12 lbs/acre with about 40 to 60 lbs/acre of TCA, generally as the ester or the salt thereof.

The concentration of the active components of this invention in their final spray solutions is not critical, though ordinarily it will be such as to provide a final spray volume that can be conveniently dispensed over the area for treatment with the particular equipment being utilized. Ordinarily spray solutions giving the required dosages as set forth above can be suitably applied by diluting the amounts of active ingredients indicated in about 150–300 gallons of liquid carrier (generally water or an oil/water emulsion).

The herbicidal products comprising Component A and Component B for use in accordance with this invention are known materials or readily available by analogy to known materials and for the most part they are commercially available as liquid or solid concentrates readily dissolved or dispersed in an appropriate liquid carrier.

The herbicidal concentrates which make up the components for use in accordance with this invention are ordinarily formulated in the form of liquid concentrates or water-dispersible or water-soluble power formulations. The spray solutions applied to the plants are obtained by dissolving or suspending the concentrates in water and diluting to volume for application. With the water-soluble agents make-up is facilitated and conveniently accomplished by including suitable surface active dispersing agents, such as anionic or nonionic emulsifying agents. The aqueous concentrates can contain one or more water miscible or water immiscible solvents. The water dispersible or water soluble concentrates can also be applied in the water phase of inverts according to techniques well known in the art.

The choice of dispersing and emulsifying agents and amounts thereof as well as other inert ingredients is dictated by the nature of the concentrate and the ease with which the active ingredient can be dispersed for final application in the liquid carrier, usually water. The liquid concentrates preferably use water as a carrier, though other liquid carriers can be used. Examples of liquid organic carriers include liquid aliphatic hydrocarbons, such as kerosene, diesel oil and the like as well as liquid aromatic hydrocarbons, such as xylene. Other liquid hydrocarbon oils, such as the various types and grades of petroleum stocks can also be utilized. Petroleum oils which are particularly suitable include the hydrocarbon mixtures of low molecular weight which are obtained by fractional distillation and which usually have a flash point between about 150°F. and 185°F. Other petroleum oils, including those generally referred to as agricultural spray oils, which are light and medium oils and consist of the fractional distillation of petroleum can also be utilized. Tall oils obtained from the sulfate digestion of wood pulp may also be employed. In some cases, where desired, formulations of this invention can also be applied in organic solvent systems such as oil-water, in which case an added herbicidal effect can be obtained from the oil carrier.

Dispersing and emulsifying agents which can be suitably employed are the condensation products of alkylene oxides, phenols and organic acids, alkylaryl sulfonates, polyoxylene derivatives of sorbitan esters, complex alcohols, phosphate esters and the like.

In the preparation of dry powder formulations the active component is dispersed in and on a finely divided solid which is non-reactive with the active agents, such as silicas, calcium silicate, carbonates, calcium phosphates, sulfur, lime, starch and the like.

The preferred concentrates of this invention are those which permit a single package combination of the Component A and Component B herbicides. A suitable formulation of such kind is a water soluble powder comprised of the sodium salts of 2,4-D and TCA combined in a ratio of about 2.5 to 5 parts of TCA for each part by weight of 2,4-D. Another preferred combination product comprises a wettable powder composition having 2,4-D and 2,4,5-T as the acids in equal proportions combined with an ester of TCA with about 4 to 5 parts of TCA for each part by weight of the 2,4-D : 2,4,5-T mixture. Salts of the herbicidal acids, used in the practice of this invention can be any of the conventional salts such as Na, K, Li, $NH_4$ and the like. Still a further example of a preferred single package liquid concentrate is an aqueous solution of the potassium salt of picloram and the sodium salt of TCA with about 10 to 40, preferably about 20, parts by weight of TCA per part of picloram.

In tests with the herbicidal combinations of this invention, TCA was employed as Component A in the form of its sodium salt or the ethylene glycol diester.

Other salts or esters could be employed with similar results as could also the acid form of 2,2-dichloropropionic acid or its salts or esters. The phenoxys 2,4-D and 2,4,5-T were generally used in the form of their glycol esters through the acid form or the esters or salts, especially the sodium, potassium, lithium or amine salts of these and the other specified phenoxys could also be employed.

EXAMPLE 1

Tests carried out, and the results obtained, with the various combination of chemicals at different concentrations and proportions are shown in Table I. The application of a 50:50 mixture of the butoxyethyl esters of 2,4-D and 2,4,5-T and the sodium salt of TCA at a concentration of 4 lbs. of the esters and 20 lbs. of TCA per 100 gallons of water was made using a No. 10 nozzle tip on an 8-gallon per minute sprayer operating at around 200 psig. pressure. The brush was up to 20 feet high. The spray, consisting of relatively large droplets, was directed under the leaf canopy or down on the foliage so that a substantial proportion of it reached the lower part of the brush and the ground.

Observations made after 3 months showed brown-out of foliage, and that sassafras was dead to the ground.

One year later there was 99% brush reduction. There was no foliage, resurge, ground cover or buds, but some canes were still green. During late August and September, some fireweed came in.

The following spring the plot looked the same, some canes were still green, but there was no resurge from the bases or along the old stems. Early during the second growing season, the canes started to desiccate rapidly and by early July, practically all were dead to ground level, maintaining the 99% brush reduction noted in the previous fall.

The fall of the second year after spraying there was still 99% of the brush killed to ground level. The ground cover was sparse. Some blueberry and sweet fern was moving in, and there was a heavy stand of fireweed present.

The fall of the third year showed 98% kill on all existing brush. Ground cover composed of sweet fern, huckleberry and grass was moving in well. In view of the elapse of over three years since treatment, the brush kill was considered as permanent and this has been confirmed by observations six years after treatment.

The treatment and results of these tests are summarized in Table I. These results demonstrate that the combinations of this invention are useful for the eradication of oaks.

Table I

Plots treated with 300 gallons per acre in July and rated in September 6 years later.

| Chemical | lbs./100 gal. | % kill |
|---|---|---|
| Trichloroacetic acid (TCA), Na Salt | 20 | 60 |
| Esters of 2,4-D and 2,4,5-T + TCA Na salt | 4 + 20 | 90 |
|  | 4 + 18 | 95 |
|  | 4 + 16 | 95 |
|  | 4 + 14 | 95 |
|  | 4 + 12 | 85 |
|  | 4 + 10 | 80 |
| Esters on foliage, TCA Na salt on ground | 4 + 20 | 98 |
| Esters of 2,4-D + 2,4,5-T + TCA Na salt | 4 + 20 | 90 |
|  | 4 + 10 | 85 |
| Ester of 2,4-D + TCA Na salt | 4 + 20 | 80 |
|  | 8 + 20 | 90 |
| Ester of 2,4,5-T + TCA Na salt | 4 + 20 | 90 |
|  | 2 + 20 | 90 |

EXAMPLE 2

A series of tests were carried out to evaluate the effectiveness against particular species with results as shown in Table II. Again the spray with this combination of chemicals was directed in such a way as to wet the foliage with most of the spray directed towards the ground. The treatment was applied at the level of 300 gal./acre.

On inspecting the plots after the elapse of 12 months it was found that the combinations when applied at optimum dose rates produced 95% kill while conventional treatments showed a significantly lower kill.

Table II

Plots treated with 300 gallons per acre in August and rated August 5 years later

| Chemical | Rate lb/100 gal | Virginia Pine | Red Maple | Sour Gum | Sassafras | Scarlet Oak | Chestnut Oak | Scrub Oak |
|---|---|---|---|---|---|---|---|---|
| Esters of 2,4-D and 2,4,5-T | 4 | 0 | 25 | 30 | 90 | 20 | 30 | 30 |
| Trichloroacetic Acid (TCA) | 20 | 50 | 30 | 80 | 80 | 40 | 50 | 50 |
| Esters of 2,4-D and 2,4,5-T + TCA | 4 + 20 | 100 | 100 | 95 | 100 | 100 | 100 | 95 |
|  | 4 + 18 | 100 | 100 | 100 | 100 | 95 | 95 | 95 |
|  | 4 + 16 | 100 | 80 | 100 | 95 | 70 | 90 | 80 |
|  | 4 + 14 | 85 | 100 | 100 | 95 | 90 | 90 | 85 |
|  | 4 + 12 | 65 | 90 | 90 | 90 | 90 | 90 | 80 |
|  | 4 + 10 | 45 | 80 | 90 | 85 | 60 | 50 | 50 |
| Esters on foliage, TCA on ground | 4 + 20 | 100 | 100 | 100 | 100 | 100 | 100 | 100 |
| Esters of 2,4-D and 2,4,5-T + TCA | 2 + 20 | 80 | 90 | 100 | 90 | 85 | 95 | 90 |
| Esters of 2,4,5-T + TCA | 2 + 20 | — | 50 | 100 | 90 | 95 | 90 | 90 |
|  | 4 + 20 | — | 90 | 95 | 80 | 90 | 95 | 85 |
| Ester of 2,4-D + TCA | 4 + 20 | — | 50 | 90 | 80 | 90 | 50 | 95 |
|  | 8 + 20 | — | 100 | 100 | 100 | 100 | 100 | 98 |

EXAMPLE 3

This test demonstrates that the use of the combined herbicidal treatment using 2,4-D and 2,4,5-T in combination as Component B and TCA as Component A for brush killing in the specified manner allows the lengthening of the spray season and the application of the spray during the early spring or late fall without any significant decrease in efficiency. The lengthening of the spray season is a definite economic advantage as it permits the use of specialized spray equipment requiring considerable investment over many more months of the year than was possible with the conventional chemical sprays and spray techniques hitherto used. The combination was applied as in examples 1 and 2, though late in the season (after September 1). Evaluations the following year and 6 years later show 95% eradication, whereas control with conventional treatments applied at the same time was diminished by more than 50% over what is obtained when applied during the growing season.

EXAMPLE 4

Table III summarizes the effect of treatments with various chemicals and combinations of chemicals at different concentrations after about 1 year and 6 years. The percentage of kill is given for all species; all oak species and the hard-to-kill scrub oak, respectively.

These data show clearly the excellent kill accomplished by the combinations of this invention, provided the herbicides are used in combination at the proper dose rates. The synergistic effect in brush killing is displayed by the combination of these two types of herbicides particularly well in the case of the oaks, since the effect of the combination of the two chemicals on oak, particularly scrub oak, when applied in accordance with the invention exceeds by far the sum of the effects shown by each component when used alone.

These tests also show that efficient brush killing is accomplished on replacing TCA with 2,2-dichloropropionic acid, provided the spray application is carried out in accordance with the novel techniques of this invention. Also, the 2,4-D and 2,4,5-T derivatives can be substituted by other chlorophenoxy derivatives or dicamba or picloram; namely 2-(2,4-dichlorophenoxy)-propionic acid (2,4-DP);
2-(2,4,5-trichlorophenoxy)-propionic acid (2,4,5-TP);
3,6-dichloro-o-anisic acid (dicamba);
4-methyl-2-chlorophenoxyacetic acid (MCPA);
4-amino-3,5,6-trichloropicolinic acid (picloram);

which can be used either as the alkali, or amine salts or in the form of esters. On using these chlorophenoxy derivatives in combination with TCA or dichloropropionic acid in accordance with the spray technique of this invention substantially complete and longlasting control of all common brush species can be accomplished.

Table III

| Herbicidal Combination | | Rate (lb/Acre) | | Percent Control | | Percent Eradication | | | Years After Application |
| --- | --- | --- | --- | --- | --- | --- | --- | --- | --- |
| Component B | Component A | Component B | Component A | All Species | Oak | All Species | Mixed Oak | Scrub Oak | |
| 2,4-D ester* + 2,4,5-T ester* (1:1) | NaTCA* | 12 | 60 | 99% | 99% | 98% | 98% | 90% | 7 |
| 2,4-D ester + 2,4,5-T ester (1:1) | NaTCA | 12 | 60 | 90% | 90% | 94% | 98% | 87% | 1 |
| | | | | | | 85% | 85% | 75% | 6 |
| 2,4-D ester + 2,4,5-T ester (1:1) | NaTCA | 12 | 60 | 98% | 98% | 98% | 98% | 95% | 1 |
| | | | | | | 95% | 90% | 85% | 6 |
| 2,4-D ester + 2,4,5-T ester + dicamba OSA* (1:1:1) | NaTCA | 18 | 60 | 99% | 99% | 98% | 99% | 98% | 1 |
| | | | | | | 99% | 98% | 98% | 6 |
| 2,4-D ester + 2,4,5-T ester (1:1) | Dalapon (sodium salt) | 12 | 12 | 75% | 75% | | | | 1 |
| 2,4-D ester + 2,4,5-T ester (1:1) | NaTCA | 12 | 60 | 99% | 99% | 97% | 98% | 94% | 6 |
| 2,4-D ester + 2,4,5-T ester (1:1) | TCA ester* | 12 | 60 | 90% | 90% | | | | 1 |
| Dicamba WSA | NaTCA | 6 | 60 | 70% | 90% | 70% | 90% | 70% | 6 |
| Dicamba OSA + 2,4-D ester + 2,4,5-T ester (2:1:1) | TCA ester | 12 | 30 | 85% | 85% | | | | 1 |
| 2,4-D ester | NaTCA | 12 | 60 | 90% | 90% | 80% | 80% | 70% | 6 |
| 2,4,5-T ester | NaTCA | 12 | 60 | 90% | 90% | 85% | 85% | 70% | 6 |
| 2,4-D ester + 2,4,5-T ester (1:1) | NaTCA | 12 | 60 | 95% | 95% | 93% | 95% | 90% | 6 |
| 2,4-D ester | NaTCA | 24 | 60 | 90% | 90% | 90% | 95% | 75% | 6 |
| Picloram (potassium salt) | NaTCA | 1.5 | 60 | 98% | 98% | | | | 1 |
| Picloram (potassium salt) | NaTCA | .75 | 60 | 95% | 95% | | | | 1 |
| Picloram (potassium salt) | TCA ester | 1.5 | 45 | 93% | 93% | | | | 1 |
| Picloram (potassium salt) | | .75 | | 40% | 40% | | | | 1 |
| 2,4-D ester + 2,4,5-T ester (1:1) | NaTCA | 12 | 60 | 95% | 95% | | | | 1 |
| 2,4-D ester | NaTCA | 24 | 60 | 90% | 90% | | | | 1 |
| 2,4-D (sodium salt)** | NaTCA | 24 | 60 | 95% | 95% | | | | 1 |
| 2,4-D (sodium salt)** | NaTCA | 24 | 60 | 90% | 95% | | | | 1 |
| 2,4-D ester + 2,4,5-T ester (1:1) | NaTCA | 12 | 60 | 98% | 98% | | | | 1 |

*2,4-D ester is the butoxyethyl ester of 2,4-D.
2,4,5-T ester is the butoxyethyl ester of 2,4,5-T.
NaTCA is the sodium salt of TCA.
Dicamba OSA is an oil soluble amine salt of dicamba.
TCA ester is ethylene glycol bis-(trichloroacetate).
Dicamba WSA is a water soluble amine salt of dicamba.
**Spray solution prepared from one package dry powder mixture of water soluble salts of 2,4-D and TCA.

EXAMPLE 5

A convenient way to use the 2,4-D and 2,4,5-T is in the form of their butoxy ethoxy esters while the TCA is used as the sodium salt. These two components can then be conveniently supplied to the users in a package containing them in separate compartments. By way of example, a package containing these components in amounts sufficient for 100 gallons of solution would need a liquid compartment for 1 gallon of the esters of 2,4-D and 2,4,5-T and a compartment for 20 lbs. of the pelleted sodium salt of TCA. This package is about the size of a 5-gallon pail. The user first dissolves the TCA in the spray tank with agitation and then adds the ester mixture. This mode of handling these chemicals avoids more expensive approaches to formulating a mixture in solid or concentrated form which is subject to deterioration. With the separate concentrates stability is not a problem since in the dilute spraying solution or emulsion they have sufficient stability to maintain their full activity and complete dispersion while the solution is being used up.

If it is desired to supply the user with a combined concentrate, TCA is provided as a concentrated aqueous solution of the sodium salt containing about 6 lbs. of the salt per gallon, or an emulsifiable TCA ester, such as ethyleneglycol bis-(trichloroacetate).

Using the ester as the source of TCA together with the esters of 2,4-D and/or 2,4,5-T, the two components of the herbicide combination can be combined into one package, and thus the user can be spared the trouble of handling two components separately.

Another way of accomplishing a one-package system of the two herbicides is to use both components in the form of alkali salts, either as a mixture of dry powder or as an aqueous solution. Thus for example the sodium salts of TCA and 2,4-D or the lithium salts of TCA, 2,4-D and 2,4,5-T can be combined in the proper proportions. Such a system preferably includes sequestering agents to prevent the precipitation of the salts, e.g., calcium and magnesium salts of 2,4-D and 2,4,5-T in hard water as well as other conventional herbicidal additaments. The lithium or potassium salts in place of the sodium salts described above can be employed if necessary to ensure better solubility.

A representative example of a dry powder water soluble concentrate for use in preparing spray solutions for the method of this invention can be conveniently formulated as follows:

|  | % by Wt. |
|---|---|
| Trichloroacetic acid, sodium salt | 66.67 |
| 2,4-D sodium salt | 29.33 |
| Aerosol OT-B (sodium sulfosuccinate wetting agent) | 0.10 |
| Polyfon 0 (sodium lignosulfonate dispersing agent) | 3.90 |

-continued

|  | % by Wt. |
|---|---|
|  | 100.00 |

The ingredients are blended until a uniform product is assured. The product must be ground so that it passes 100% through a 20 mesh screen.

In the foregoing examples I have described several versions and embodiments of my invention. However, on the basis of these descriptions those versed in the art can design and deduce many other combinations of spraying techniques, herbicidal combinations and formulations for effective and lasting brush killing provided a combination of chemicals selected from each of the two groups of herbicides is applied in accordance with my invention. Accordingly, the scope of my invention is not limited by the specific modes of execution and particular formulations disclosed above, except as it is defined by the claims that follow.

I claim:

1. In the process of eradicating oak plants with a combined effective amount of A) trichloroacetic acid, its conventional salts and esters and B) a mixture containing equal proportions of 2,4-dichlorophenoxyacetic acid and 2,4,5-trichlorophenoxyacetic acid, their conventional salts and esters, the improvement consisting of applying onto the ground and over the root systems of said plants component A and applying to the foliage or upper portions of said plants component B wherein component A is applied in a ratio of about 2.5 to 5 parts for each part of component B.

2. The method of claim 1 wherein A and B are applied simultaneously so as to cause the upper portions of said plants to be moistened while the bulk of the material is applied to the ground and root systems of said plants.

3. The method of claim 2 wherein component A is sodium TCA and component B is the butoxyethyl ester of 2,4-D and 2,4,5-T respectively.

4. The method of claim 1 wherein component A is sodium TCA and component B is the butoxyethyl ester of 2,4-D and 2,4,5-T respectively.

* * * * *